(12) United States Patent
Malhi et al.

(10) Patent No.: US 8,758,282 B2
(45) Date of Patent: *Jun. 24, 2014

(54) COMPRESSION GARMENT APPARATUS HAVING SUPPORT BLADDER

(75) Inventors: Arnaz S. Malhi, Watertown, MA (US); Manish Deshpande, Canton, MA (US)

(73) Assignee: Covidien LP, Mansfield, MA (US)

( * ) Notice: Subject to any disclaimer, the term of this patent is extended or adjusted under 35 U.S.C. 154(b) by 511 days.

This patent is subject to a terminal disclaimer.

(21) Appl. No.: 12/893,683

(22) Filed: Sep. 29, 2010

(65) Prior Publication Data

US 2012/0078145 A1 Mar. 29, 2012

(51) Int. Cl.
*A61H 7/00* (2006.01)

(52) U.S. Cl.
USPC ............ 601/151; 601/149; 601/150; 601/152

(58) Field of Classification Search
USPC ........... 601/23, 24, 26, 27, 33, 35, 75, 84, 85, 601/88, 90, 92, 93, 96, 97, 98, 101, 103, 601/105, 107, 108, 133, 134, 148–152; 601/DIG. 7; 602/13; 606/201, 202; 128/DIG. 20
See application file for complete search history.

(56) References Cited

U.S. PATENT DOCUMENTS

| | | |
|---|---|---|
| 3,892,229 A | 7/1975 | Taylor et al. |
| 3,901,221 A | 8/1975 | Nicholson et al. |
| 4,013,069 A | 3/1977 | Hasty |
| 4,206,751 A | 6/1980 | Schneider |
| 4,624,244 A * | 11/1986 | Taheri ............................. 601/152 |
| 4,986,260 A | 1/1991 | Iams et al. |
| 5,007,411 A | 4/1991 | Dye |
| 5,109,832 A | 5/1992 | Proctor et al. |
| 5,117,812 A | 6/1992 | McWhorter |
| 5,139,475 A * | 8/1992 | Robicsek ......................... 602/13 |
| 5,186,163 A * | 2/1993 | Dye ................................ 601/27 |
| 5,218,954 A | 6/1993 | van Bemmelen |
| 5,263,473 A | 11/1993 | McWhorter |
| 5,443,440 A | 8/1995 | Tumey et al. |
| 5,517,999 A | 5/1996 | Newell |
| 5,520,622 A | 5/1996 | Bastyr et al. |
| 5,701,894 A | 12/1997 | Cherry et al. |

(Continued)

FOREIGN PATENT DOCUMENTS

| | | |
|---|---|---|
| CA | 2411046 C | 11/2008 |
| CN | 1794964 A | 6/2006 |

(Continued)

OTHER PUBLICATIONS

European Search Report regarding related application serial No. EP 11182432.2 dated Mar. 28, 2012, 6 pgs.

(Continued)

*Primary Examiner* — Steven Douglas
(74) *Attorney, Agent, or Firm* — John Paul Mello, Esq.

(57) ABSTRACT

A compression garment apparatus includes a compression garment and a pressurizer. The pressurizer intermittently pressurizes a therapeutic bladder on the compression garment and pressurizes a support bladder on the compression garment to enhance the fit of the compression garment and maintain the therapeutic bladder in position with respect to a target compression zone on a body part on which the garment is worn. The support bladder may be selectively pressurized when needed based at least in part on sensed physical characteristics.

24 Claims, 9 Drawing Sheets

(56) References Cited

U.S. PATENT DOCUMENTS

| | | |
|---|---|---|
| 5,827,209 A | 10/1998 | Gross |
| 5,855,589 A | 1/1999 | McEwen et al. |
| 5,891,065 A | 4/1999 | Cariapa et al. |
| 5,982,285 A | 11/1999 | Bueche et al. |
| 6,007,559 A | 12/1999 | Arkans |
| 6,209,144 B1 | 4/2001 | Carter |
| 6,290,662 B1 | 9/2001 | Morris et al. |
| 6,306,088 B1 | 10/2001 | Krausman et al. |
| 6,322,528 B1 | 11/2001 | Kania |
| 6,338,723 B1 * | 1/2002 | Carpenter et al. .............. 602/75 |
| 6,368,357 B1 | 4/2002 | Schon et al. |
| 6,409,691 B1 | 6/2002 | Dakin et al. |
| 6,494,852 B1 * | 12/2002 | Barak et al. ................... 601/151 |
| 6,540,707 B1 | 4/2003 | Stark et al. |
| 6,544,202 B2 | 4/2003 | McEwen et al. |
| 6,544,203 B2 | 4/2003 | Hazard |
| 6,558,338 B1 * | 5/2003 | Wasserman ................... 601/152 |
| 6,656,141 B1 | 12/2003 | Reid |
| 7,056,297 B2 | 6/2006 | Dohno et al. |
| 7,204,809 B2 | 4/2007 | Hung |
| 7,254,516 B2 | 8/2007 | Case, Jr. et al. |
| 7,270,642 B2 | 9/2007 | Ouchene et al. |
| 7,503,878 B1 | 3/2009 | Amsbury et al. |
| 7,811,333 B2 | 10/2010 | Jonsson et al. |
| 7,871,387 B2 | 1/2011 | Tordella et al. |
| 7,947,003 B2 * | 5/2011 | Bonnefin et al. .............. 601/150 |
| 7,967,766 B2 * | 6/2011 | Ravikumar ..................... 602/13 |
| 8,162,861 B2 * | 4/2012 | Avitable et al. ............... 601/151 |
| 2002/0104535 A1 | 8/2002 | Biondo et al. |
| 2004/0199090 A1 | 10/2004 | Sanders et al. |
| 2005/0107725 A1 | 5/2005 | Wild et al. |
| 2006/0036203 A1 | 2/2006 | Ouchene et al. |
| 2006/0287621 A1 | 12/2006 | Atkinson et al. |
| 2007/0049853 A1 | 3/2007 | Adams et al. |
| 2007/0135742 A1 | 6/2007 | Meyer et al. |
| 2007/0270665 A1 | 11/2007 | Yang et al. |
| 2008/0082029 A1 | 4/2008 | Diana |
| 2008/0125684 A1 | 5/2008 | Nardi et al. |
| 2008/0132816 A1 | 6/2008 | Kane et al. |
| 2009/0024062 A1 | 1/2009 | Einarsson |
| 2009/0076423 A1 | 3/2009 | Reeves et al. |
| 2009/0088674 A1 | 4/2009 | Caillouette et al. |
| 2009/0118651 A1 | 5/2009 | Rousso et al. |
| 2009/0177222 A1 | 7/2009 | Brown et al. |
| 2010/0010405 A1 | 1/2010 | Nardi et al. |
| 2010/0081974 A1 | 4/2010 | Vess |
| 2010/0081977 A1 | 4/2010 | Vess |
| 2011/0190675 A1 * | 8/2011 | Vess .............................. 601/152 |

FOREIGN PATENT DOCUMENTS

| | | |
|---|---|---|
| CN | 101267793 A | 9/2008 |
| DE | 102006033033 A1 | 1/2008 |
| EP | 1980232 A1 | 10/2008 |
| EP | 2359785 A1 | 8/2011 |
| JP | 07-250875 A | 10/1995 |
| JP | 2000-197675 A | 7/2000 |
| JP | 3107269 U | 1/2005 |
| JP | 2006-521142 A | 9/2006 |
| JP | 2008-136587 A | 6/2008 |
| KR | 10-0918718 A | 10/2008 |
| WO | 0049968 A2 | 8/2000 |

OTHER PUBLICATIONS

Exam Report issued Jun. 29, 2012 in related Australian application No. 2011221374, 5 pgs.

English Translation of Preliminary Rejection issued Nov. 16, 2012 in corresponding Korean Patent Application No. 10-2011-98803, 3 pgs.

English Translation of Notice of Reasons for Rejection issued Dec. 28, 2012 in corresponding Japanese Patent Application No. 2011-211028, 5 pgs.

Exam Report dated Apr. 19, 2013 from related Canadian Patent Application Serial No. 2751347, 3 pages.

Office Action in related Korean Application No. 10-2011-98803 dated May 27, 2013, 3 pages. (English Translation).

Office Action in related Canadian Application No. 2751347, dated Dec. 16, 2013, 2 pages.

Office Action in related Chinese Application No. 201110303799.8, dated Oct. 29, 2013, 10 pages. (English Translation).

* cited by examiner

COMPRESSION GARMENT APPARATUS HAVING SUPPORT BLADDER

FIELD OF THE INVENTION

The present invention generally relates to a compression garment apparatus, and more particularly to a compression garment apparatus including a therapeutic bladder and a support bladder.

BACKGROUND OF THE INVENTION

A major concern for generally immobile patients and like persons are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popliteal and tibial return deoxygenated blood to the heart. For example, when blood circulation in these veins is retarded due to illness, injury or inactivity, there is a tendency for blood to accumulate or pool. A static pool of blood may lead to the formation of a blood clot, which can interfere with cardiovascular circulation. Most seriously, a fragment of the blood clot can break loose and migrate. A pulmonary embolus can form from the fragment potentially blocking a main pulmonary artery, which may be life threatening. The current invention can also be applied to the treatment of other conditions, such as lymphedema.

Conventional vascular compression systems include a compression garment fluidly connected to a controller for cyclically inflating the compression garment. The cyclical inflation of the compression garment enhances blood circulation and decreases the likelihood of DVT. A system of conduits connects the compression garment to the controller. Newer vascular compression garments have portable controllers that are much smaller and even mountable on the compression garment so that the patient may move about freely without having to first remove the compression garment or disconnect the compression garment from a controller. These new compression garments may be worn when a patient is stationary or ambulatory and enhance patient compliance because of convenience of use.

Active compression garments for applying intermittent compression therapy to a body part (e.g., a limb such as a leg) have many applications, including deep vein thrombosis (DVT) prophylaxis, edema prevention, and aiding in wound healing. The performance of such compression garments is sensitive to the ability of the garment to retain its initial fit or tightness and the inflatable bladders to retain their original position around the body part. This can be very difficult when the compression garments are used during and after ambulation, such as walking, sitting, standing, and rolling over. The garments tend to loosen around the body part or slide down the body part causing misalignment of inflatable bladders with corresponding body parts, which may result in ineffective compression therapy and/or discomfort. The present invention is directed to maintaining desired fit of the garment on the body part and maintaining the inflatable bladders in position with respect to a target compression zone on the body part to improve applied compression therapy.

SUMMARY OF THE INVENTION

One aspect of the present invention is directed to a compression garment apparatus including a compression garment having an inflatable therapeutic bladder and an inflatable support bladder. The compression garment is selectively positionable on a body part so the therapeutic bladder covers a target compression zone on the body part. The compression garment apparatus further includes a pressurizer operatively connectable to the therapeutic bladder and the support bladder for selectively pressurizing the bladders by increasing gas pressure within the bladders. The pressurizer includes a sensor for sensing and generating signals representative of at least one physical characteristic selected from a group of characteristics consisting of an orientation of the body part, a motion of the body part, an acceleration of the body part, a motion of the garment relative to the target compression zone, a pressure in the therapeutic bladder, a pressure in the support bladder, a gas volume in the therapeutic bladder, and a gas volume in the support bladder. The pressurizer further includes a controller operatively connected to the sensor. The controller cyclically directs pressurized gas to the therapeutic bladder to provide intermittent compression therapy to the target compression zone on the body part and directs pressurized gas to the support bladder in response to signals received from the sensor representing the physical characteristic to maintain the therapeutic bladder in position with respect to the target compression zone.

Another aspect of the present invention is direct to a method of providing compression therapy on a target compression zone of a body part of a human. The method includes covering the target compression zone of the body part with a compression garment having an inflatable therapeutic bladder and an inflatable support bladder. The method further includes sensing at least one characteristic selected from a group of characteristics consisting of an orientation of the body part, a motion of the body part, an acceleration of the body part, a motion of the garment relative to the target compression zone, a pressure in the therapeutic bladder, a pressure in the support bladder, a gas volume in the therapeutic bladder, and a gas volume in the support bladder. The support bladder is pressurized in response to the sensed characteristic to maintain the therapeutic bladder in position with respect to the target compression zone. The therapeutic bladder is cyclically pressurized to provide intermittent compression therapy to the target compression zone of the body part.

Another aspect of the present invention is directed to a compression garment apparatus including an inflatable therapeutic bladder sized and shaped for covering a target compression zone on a body part. The compression garment further includes an inflatable support bladder connected to the therapeutic bladder for holding the therapeutic bladder in position with respect to the target compression zone. A pressurizer is operatively connected to the therapeutic bladder and the support bladder. The pressurizer also pressurizes the support bladder to hold the therapeutic bladder in position and cyclically pressurizing the therapeutic bladder to provide intermittent compression therapy to the target compression zone on the body part.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
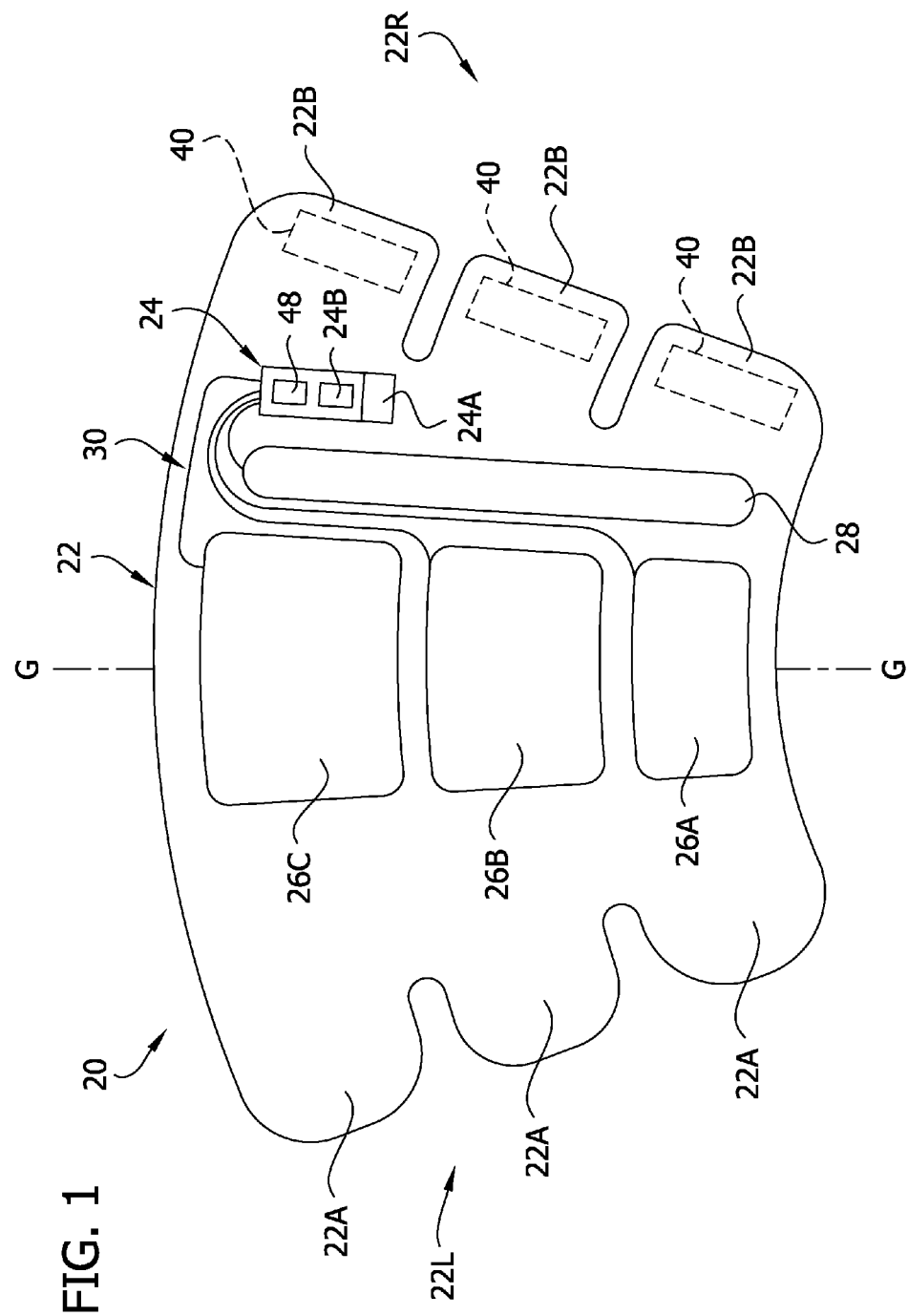
FIG. 1 is a plan view of a compression garment apparatus of the present invention shown in an open, unwrapped configuration.

Referring to the drawings and in particular to FIGS. 1-4, a compression garment apparatus for applying compression therapy to a body part of a wearer is generally indicated 20. As will be explained in detail hereinafter, the compression garment apparatus 20 may be used for intermittently compressing a body part such as a limb (e.g., a leg or arm). The body part referred to herein and shown throughout the drawings is a leg, generally designated L.

The compression garment apparatus 20 includes a compression garment, generally indicated by 22, and a pressurizer, generally indicated by 24. The compression garment 22 includes three therapeutic bladders 26A-26C and a support bladder 28. As described in more detail below, the pressurizer 24 intermittently pressurizes the therapeutic bladders 26A-26C to impart compression therapy on the body part L and pressurizes the support bladder 28 to maintain the therapeutic bladders in position with respect to the body part. The pressurizer 24 is operatively connected to the bladders 26A-26C, 28 such as by conduits 30 (FIG. 1) for inflating the bladders. The illustrated pressurizer 24 is mounted on the compression garment 22. A configuration in which a pressurizer is removably mounted on a compression garment and operatively connected to bladders on the compression garment is disclosed in more detail in U.S. patent application Ser. No. 12/241,670 (Vess) and U.S. patent application Ser. No. 12/241,936 (Vess), which are both assigned to Tyco Healthcare Group LP and hereby incorporated by reference in their entireties. Other embodiments, such as where the pressurizer 24 is not configured for mounting on the compression garment 22 are within the scope of the present invention.

The compression garment 22 is selectively positionable on the body part L so that the therapeutic bladders 26A-26C cover or overlie a target compression zone T on the body part. The target compression zone T may be any portion of the body part L upon which it is desired to impart compression therapy. For example, a target compression zone on the leg may comprise generally a rear side of the leg L or a particular portion thereof such as the calf or the rearward part of the thigh. The rear side of the leg L includes calf and thigh muscles through which veins pass and compression of which enhances flow of blood in those veins. Other target compression zones may be used such as a portion of the rear of the leg or a larger portion of the leg.

Figure 3:
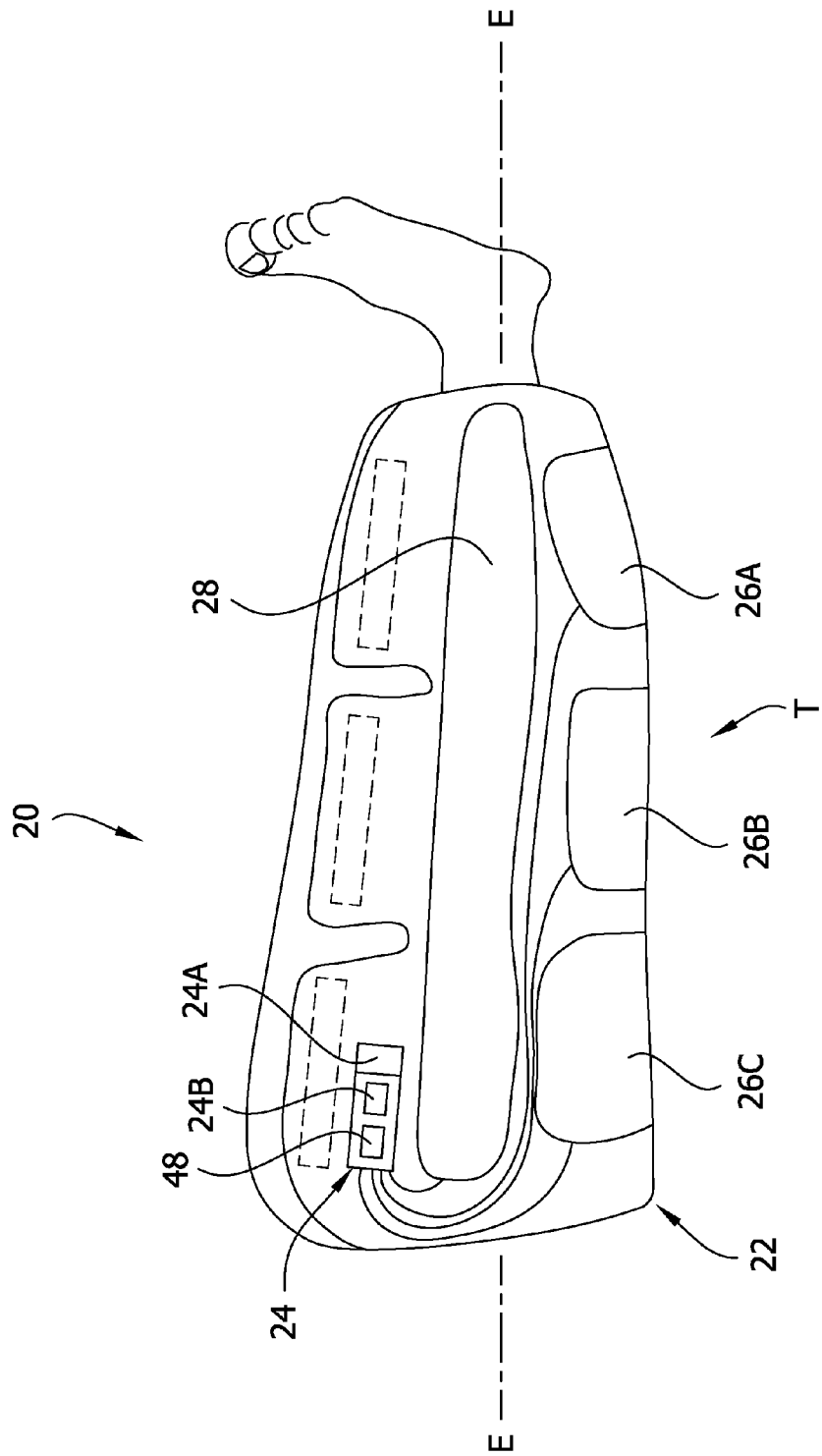
FIG. 3 is a side elevation of the compression garment apparatus on the leg in a generally horizontal orientation, a support bladder of the compression garment apparatus being shown in a pressurized state.

The illustrated compression garment 22 has a "thigh length" size, i.e., the compression garment extends generally from the ankle to the thigh. As shown in FIG. 3, the therapeutic bladders 26A-26C are positioned on the garment 22 to generally overlie the rear side of the leg L, and more particularly, the ankle, calf, and thigh, respectively. The three therapeutic bladders 26A-26C are arranged in sequence along the leg L. Other sizes and shapes of garments 22 (e.g., "knee length," extending generally from the ankle to below the knee) or having different configurations of therapeutic bladders 26A-26C (e.g., one, two, or more therapeutic bladders) are within the scope of the present invention.

The compression garment 22 may be placed in a self-retaining configuration on the leg L by positioning the therapeutic bladders 26A-26C over the desired target compression zone T and wrapping the compression garment around the leg such that opposite sides of the compression garment 22L, 22R (FIG. 1) overlap each other. A generally tight or snug fit is desirable so that pressurization of the therapeutic bladders 26A-26C causes compression of the body part L. The illustrated compression garment 22 includes corresponding straps 22A, 22B on each side 22L, 22R of the compression garment to facilitate tightening and securing of the compression garment. The compression garment 22 is tightened around the leg L by pulling and overlapping the opposite sides 22L, 22R of the compression garment. The compression garment 22 may be secured about the leg L by fasteners 40. For example, the fasteners 40 in the illustrated embodiment comprise sections of hook fabric (also designated 40) on the straps 22B for fastening to loop fabric on an outside surface of the compression garment 22C (FIG. 2). Compression garments having other configurations capable of selective positioning on a body part for placement of a therapeutic bladder with respect to a target compression zone are within the scope of the present invention.

Figure 2:
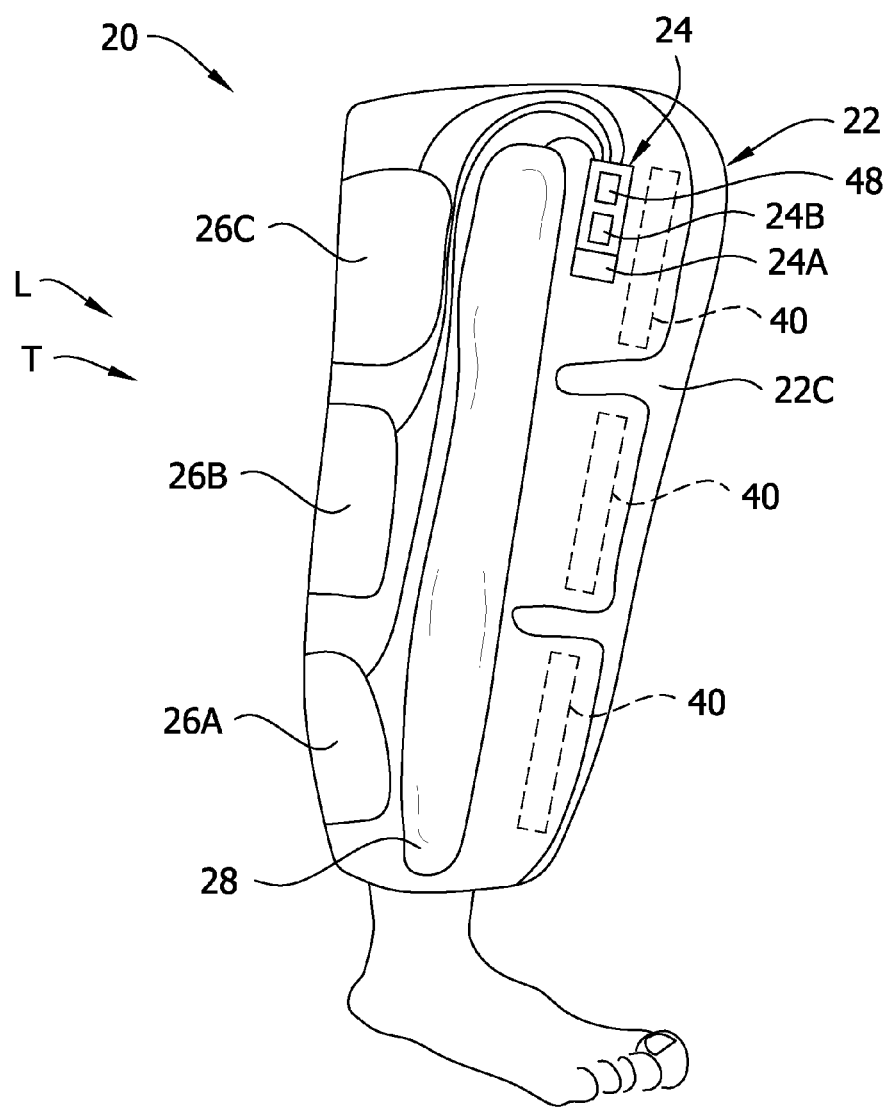
FIG. 2 is a side perspective of the compression garment apparatus on a leg.

The illustrated support bladder 28 comprises an elongate bladder extending along the length of the compression garment 22 generally parallel to a longitudinal axis G-G of the garment (FIG. 1). The support bladder 28 is sized and shaped to extend longitudinally along the leg L (generally parallel to a longitudinal axis E-E of the leg (FIG. 3)) when the compression garment 22 is worn. As shown in FIG. 2, in use the support bladder 28 is positioned on the compression garment 22 so the bladder extends along the outer side of the leg L. The support bladder 28 extends from near the ankle to above the knee. When pressurized, the support bladder 28 provides structural support to the compression garment 22. The support bladder 28 provides rigidity to the compression garment 22 relative to the general flexible nature of the garment. For example, the support bladder 28 may provide sufficient rigidity to the compression garment 22 to cause the compression garment to "stay up" on the leg (i.e., not "fall down" onto itself) when the wearer is standing. However, pressure within the support bladder 28 desirably is prevented from exceeding a pressure at which the support bladder is generally compliant to movement of the body part L. In other words, the support bladder 28 desirably does not provide substantially rigid support or impede general movement of the leg L such as bending at the knee. The support bladder 28 is not used to make the compression garment 22 into a rigid brace for the body part L on which it is worn. When pressurized, the support bladder 28 maintains inside surfaces of the compression garment 22 in contact with outside surfaces of the leg L to provide friction for preventing the compression garment from moving with respect to the leg. The support bladder 28 may be configured to expand inwardly, toward the leg L, to fill space between the leg and the compression garment to create a tighter fit. The tighter fit increases friction between the compression garment 22 and the leg L. Embodiments in which the support bladder 28 has a different configuration or in which two, three, four, or more support bladders are used are within the scope of the present invention.

The compression garment 22 may be constructed in various ways known in the art. In one construction, the garment 22 is formed of opposing inner and outer sheets of a generally flexible, fluid impervious material (e.g., PVC) that are welded together along bladder lines to form the bladders 26A-26C, 28. Alternatively, the bladders 26A-26C, 28 may be formed separately and mounted on the compression garment 22.

The pressurizer 24 intermittently pressurizes the therapeutic bladders 26A-26C to provide compression therapy to the leg L. The pressurizer 24 includes a source of pressurized or compressed gas 24A (e.g., a battery-powered pump) and a controller 24B for directing the pressurized gas to the bladders 26A-26C, 28 as desired. The controller 24B may include a microprocessor and suitable valving (not shown). The controller 24B cyclically directs pressurized gas to the therapeutic bladders 26A-26C to provide intermittent compression therapy to the target compression zone T. For example, the controller 24B directs pressurized gas to the therapeutic bladders 26A-26C to cyclically pressurize the therapeutic bladders in sequence (e.g., ankle to thigh) to peristaltically enhance flow of bodily fluids. The controller 24B may be configured and programmed to execute various other intermittent inflation routines, all of which are within the scope of the present invention.

As explained above, the pressurizer 24 pressurizes the support bladder 28 to maintain the desired fit of the compression garment and/or maintain the position of the therapeutic bladders 26A-26C with respect to the target compression zone T. The controller 24B desirably prevents gas pressure in the support bladder 28 from exceeding a pressure at which stasis occurs. The pressure within the support bladder 28 may be maintained at a predetermined constant or baseline pressure, or the bladder may be selectively pressurized (i.e., pressurized when necessary). Maintaining constant pressure in the support bladder 28 may cause discomfort to the wearer. For example, the support bladder 28 may create skin irritation or pressure on the leg L that becomes uncomfortable after extended exposure. Moreover, the tight fit caused by the support bladder 28 may hinder air circulation between the garment and the leg L, causing retention of body heat and possible accumulation of perspiration. Accordingly, it may be desirable to pressurize the support bladder 28 selectively, i.e., in situations in which the support bladder is necessary, so that the support bladder is generally unpressurized or pressurized at a low level at times when pressurization in the support bladder is generally not necessary.

To facilitate selective pressurization of the support bladder 28, the pressurizer includes one or more sensors 48 operatively connected to the controller 24B. The sensor 48 senses physical characteristics relevant to pressurization of the support bladder 28. For example, the sensor 48 may be adapted to sense orientation of the body part L, motion of the body part, motion of the garment 22 relative to the target compression zone T, pressure in the therapeutic bladders 26A-26C, pressure in the support bladder 28, gas volume in the therapeutic bladders, and/or gas volume in the support bladder. Such characteristics are explained in more detail below. The sensor 48 generates signals indicative of such characteristics which are communicated to the controller 24B. The controller 24B pressurizes the support bladder 28 based at least in part on signals received from the sensor 48. The illustrated sensor 48 is provided on the pressurizer 24, but the sensor 48 may be separate from the pressurizer and mounted separately on the compression garment 22 or located elsewhere on the wearer. Various types of sensors 48 may be used. For example, accelerometers and other sensors based on capacitive, piezoresistive, piezoelectric, Hall effect, magnetorestrictive, resonant beam, or other technologies may be used.

Figure 4:
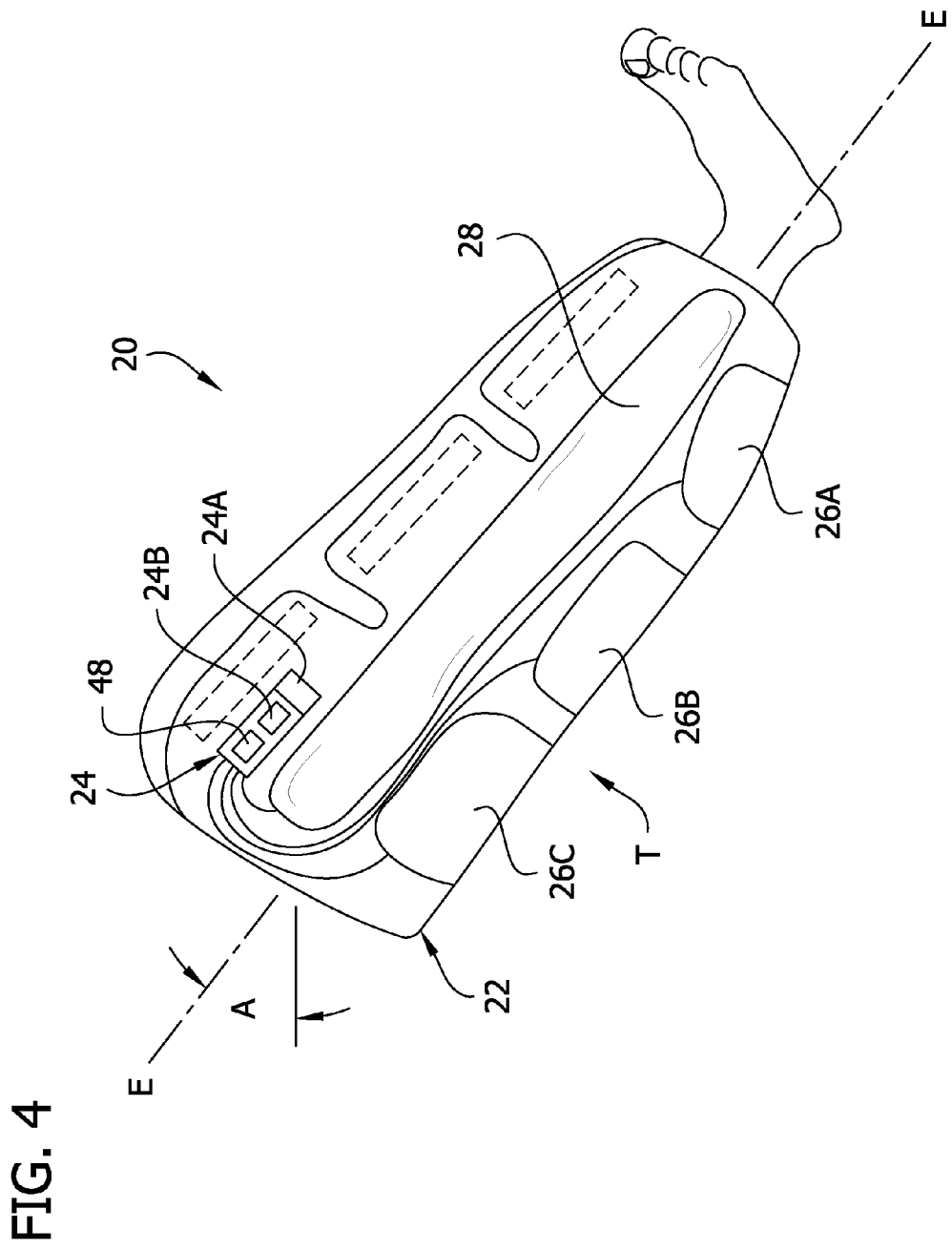
FIG. 4 is a side elevation of the compression garment apparatus on the leg in an inclined orientation, the support bladder being shown in a pressurized state.

In FIG. 3, the leg L is shown in a generally horizontal position, and the support bladder 28 is shown in a generally low pressure or unpressurized state. The position of the leg L in FIG. 3 represents a possible position of the leg when the wearer of the compression garment is lying in a bed. The support bladder 28 may not require pressure or require a minimal amount of pressure in this position to maintain the desired fit of the garment 22 on the leg L or the desired position of the therapeutic bladder 26A-26C with respect to the target compression zone T. If the wearer were to, for example, roll over in bed or change the orientation of their leg L, increased pressure within the support bladder 28 may be desirable to prevent the therapeutic bladders 26A-26C from moving with respect to the target compression zone T. FIGS. 2 and 4 show the support bladder 28 in a pressurized state.

The controller 24B may pressurize the support bladder 28 based on sensed limb orientation. For example, the controller 24B may direct pressurized gas to the support bladder 28 in response to a signal received from the sensor 48 indicating the orientation of the body part L is beyond a threshold orientation or outside a predetermined orientation range. The support bladder 28 may be pressurized when the longitudinal axis E-E of the leg is at least 30 degrees with respect to horizontal (e.g., angle A in FIG. 4). Other threshold orientations may be used, such as 40, 50, 60, 70, or 80 degrees with respect to horizontal. Alternatively, the support bladder may be pressurized when the longitudinal axis E-E of the leg is outside a predetermined orientation range such as 0-30, 0-40, 0-50, 0-60, 0-70, or 0-80 degrees with respect to horizontal. Moreover, the support bladder 28 may be pressurized when the sensor 48 indicates the leg L is generally upright (e.g., FIG. 2), and the pressure in the support bladder 28 may be vented when the leg is recumbent (e.g., FIG. 3). The tilt angle of the body part L may be determined using an accelerometer as the sensor 48. Signals from the accelerometer 48 are filtered using software or hardware to recognize acceleration due to tilt angle, which is measured and evaluated by the controller 24B. The sensor 48 may also be used to sense angular orientation of the leg L (i.e., bending at the knee), in which case two sensors 48 may be necessary. For example, a first sensor may be positioned adjacent the thigh portion, a second sensor may be positioned adjacent the ankle portion, and proximity of the two sensors may be monitored to determine angle (not shown). The pressure in the support bladder 28 may be reduced when orientation of the leg L approaches horizontal or after the leg remains generally horizontal for a predetermined amount of time.

The controller 24B may also pressurize the support bladder 28 based on sensed movement of the garment 22 relative to the target compression zone T. For example, the sensor 48 may be adapted to sense motion of the garment 22 longitudinally or circumferentially about the leg L. Such a sensor 48 may be positioned on an inside surface of the compression garment (not shown) to sense movement along the surface of the leg L. Moreover, two sensors 48 may be used, for example, one on the garment and one elsewhere on the wearer, and the positions of the sensors be monitored with respect to each other. Such an arrangement could be used to monitor motion in the form of bending at the knee.

The controller 24B may also pressurize the support bladder 28 based on sensed limb movement or acceleration. The need for the compression garment 22 to have a good fit on the leg L is increased when the wearer is moving in bed or ambulating because the garment may tend to slip or slide on the leg during movement of the leg. The controller 24B may direct pressurized gas to the support bladder 28 in response to a signal received from the sensor 48 indicating the motion or acceleration of the body part L is beyond a threshold amount of motion or acceleration or outside a predetermined acceleration range. For example, the support bladder 28 may be pressurized when the sensor 48 indicates the limb L is moving more than a predetermined minimum amount. Moreover, the support bladder 28 may be pressurized when the sensor 48 indicates the wearer is ambulating. For example, the sensor 48 may be an accelerometer and the controller 24B may be programmed to determine when the wearer is walking using "step counting," where the controller 24B recognizes a step each time a change in slope of the vertical axis acceleration occurs. Alternatively, a GPS tracker 48 may be used for sensing movement and triggering pressurization of the support bladder 28 based on movement. Other types of sensors may be used to detect motion and acceleration. The pressure in the support bladder 28 may be reduced immediately or a predetermined amount of time after movement or acceleration is no longer sensed.

Moreover, the controller 24B may pressurize the support bladder 28 based on pressure achieved or gas volume achieved in one of the therapeutic bladders 26A-26C during a cycle of inflation. Failure to achieve a desired pressure in one of the therapeutic bladders 26A-26C during an inflation cycle may indicate the fit of the compression garment 22 is loose. In response, the controller 24B may increase the pressure within the support bladder 28, which would in turn tighten the fit of the compression garment 22 about the leg, and would result in increased pressure in the therapeutic bladders (assuming the same volume of gas) and achievement of desired compression on the limb in the next compression cycle. An excessive amount of gas volume sensed in one of the therapeutic bladders 26A-26C may also indicate the fit of the compression garment 22 is loose, if the controller 24B is programmed to inflate the therapeutic bladder automatically to a pressure to impart a desired amount of compression on the limb L. In response, the controller 24B may pressurize the support bladder 28, which would decrease the volume of gas required to achieve the desired compression on the limb L and thus decrease the volume of gas achieved in the therapeutic bladder in the following compression cycle.

The controller 24B may pressurize the support bladder 28 based on pressure or gas volume in the support bladder 28. In some embodiments, it may be desirable to maintain a constant or baseline pressure in the support bladder 28 instead of selectively pressurizing the support bladder. The pressure or gas volume in the support bladder 28 may be monitored by the sensor 48, which signals the controller 24B if the pressure needs to be increased or decreased to maintain the constant or baseline pressure.

Selective pressurization of the support bladder 28 may be carried out in different modes. For example, pressurization of the support bladder 28 may be "all or nothing." In other words, when the support bladder 28 is selectively pressurized, it is either pressurized at a predetermined, constant pressure or is generally unpressurized or pressurized at a baseline pressure. Alternatively, the support bladder 28 may be pressurized incrementally. For example, the pressure in the support bladder 28 may be increased by 1 mmHg for every increment of change of orientation (e.g., every 10 degrees) with respect to horizontal, for incremental change in magnitude or speed of movement (e.g., every 0.1 meters per second), or for incremental change in acceleration.

In a cycle of use, the compression garment apparatus 20 is placed on a body part such as the leg L, with the therapeutic bladders 26A-26C covering or overlying the desired target compression zone T. The pressurizer 24 intermittently pressurizes the therapeutic bladders 26A-26C to impart compression therapy. The pressurizer also pressurizes the support bladder 28 constantly or selectively (e.g., based on sensed physical characteristics) to maintain the desired fit of the compression garment 22 on the body part L and maintain the therapeutic compression bladders 26A-26C in position with respect to the target compression zone T.

Figure 5:
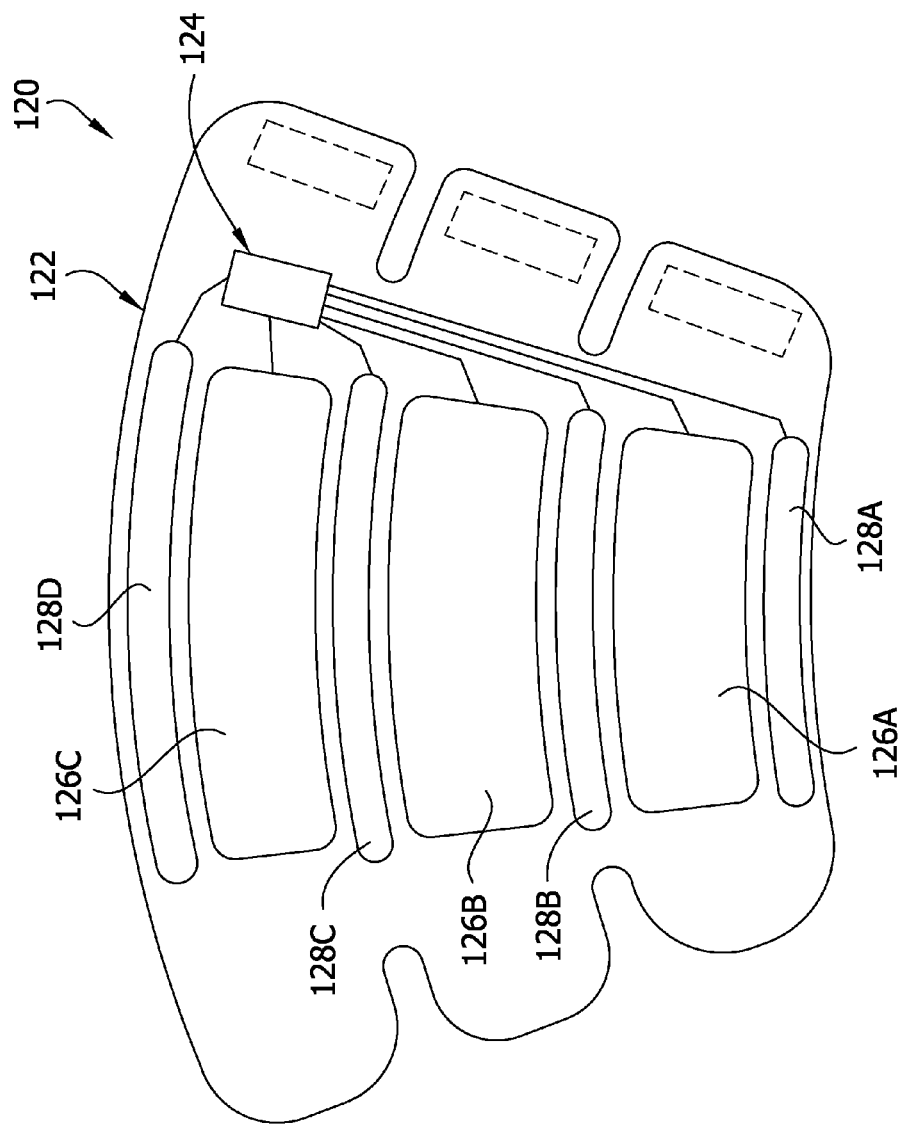
FIG. 5 is a plan view of a second embodiment of a compression garment apparatus of the present invention.
Figure 6:
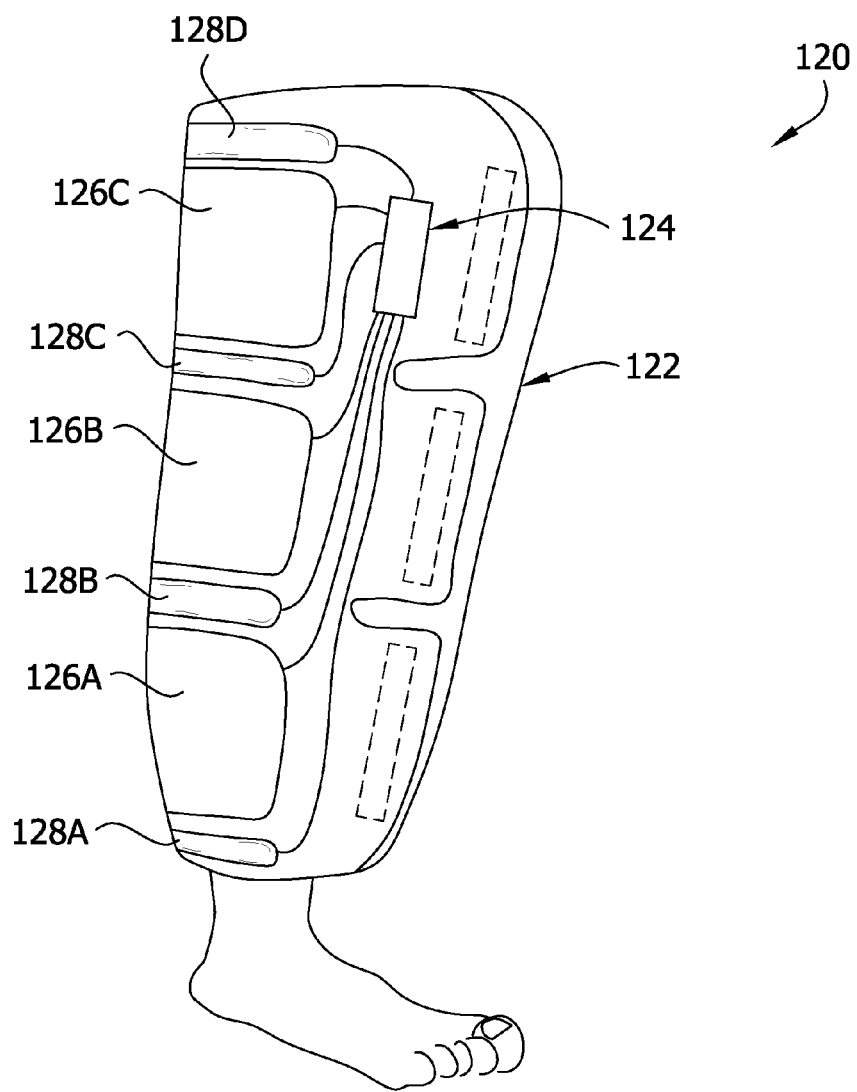
FIG. 6 is a side elevation of the compression garment apparatus of FIG. 5, a support bladder on the compression garment apparatus being shown in a pressurized state.

FIGS. 5 and 6 illustrate a second embodiment of a compression garment apparatus 120 of the present invention. The compression garment apparatus 120 is similar to the compression garment apparatus 20 described above, and corresponding parts are generally indicated by the same reference numbers, plus 100. This embodiment includes four support bladders 128A-128D, which are positioned so they extend circumferentially about the body part L when the compression garment 122 is worn. The illustrated support bladders 128A-128D are positioned above, below, and between the therapeutic bladders 126A-126C. In use, the pressurizer 124 may pressurize the therapeutic bladders 126A-126C and support bladders 128A-128D as described above.

Figure 7:
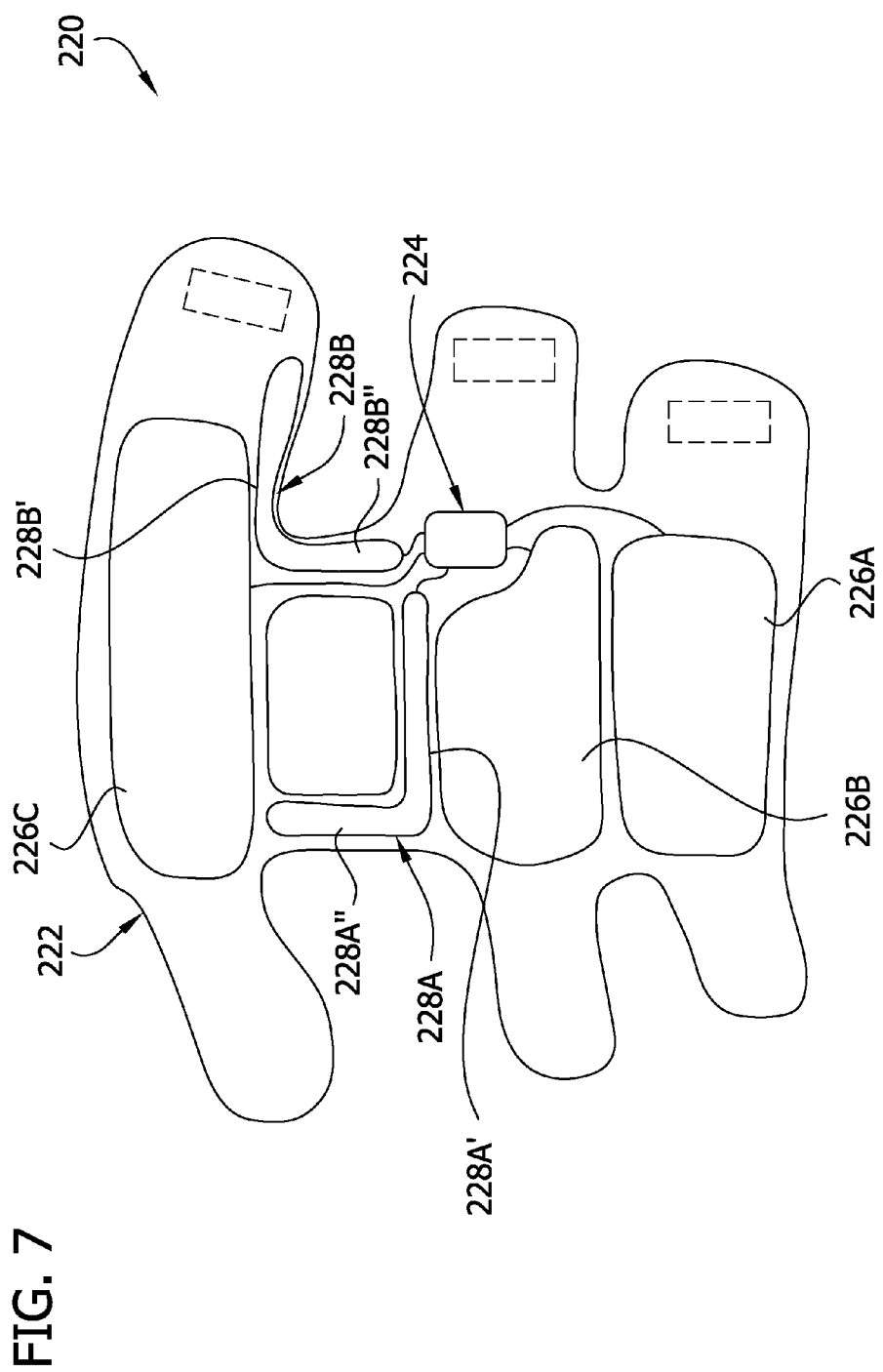
FIG. 7 is a plan view of a third embodiment of a compression garment apparatus of the present invention.
Figure 8:
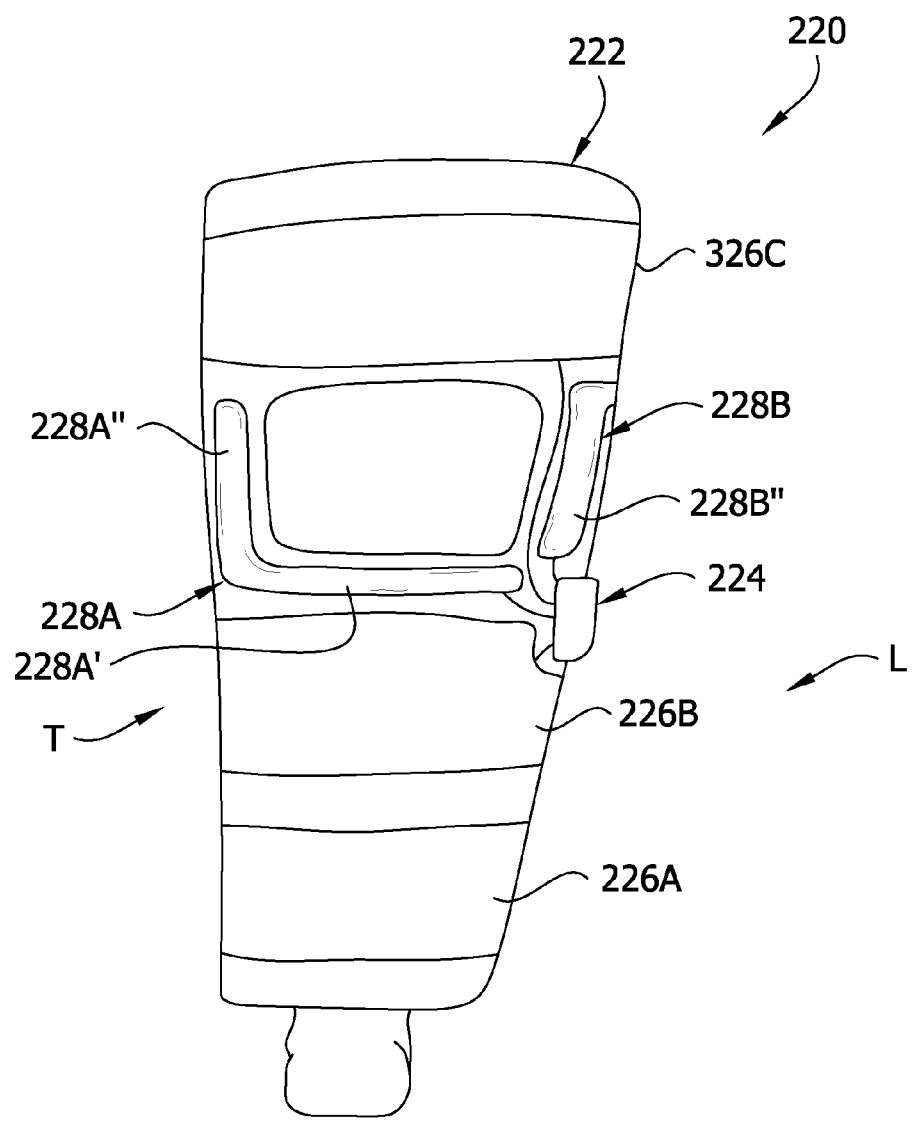
FIG. 8 is a rear elevation of the compression garment apparatus of FIG. 7, support bladders on the compression garment apparatus being shown in a pressurized state.
Figure 9:
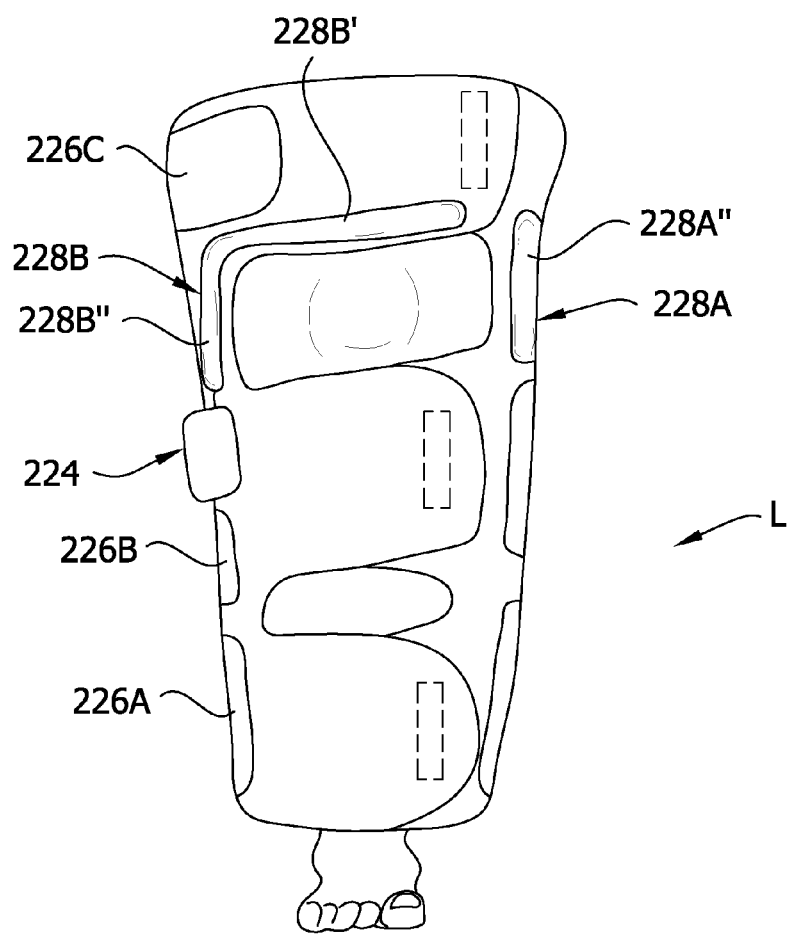
FIG. 9 is a front elevation of the compression garment apparatus of FIG. 8.

FIGS. 7-9 illustrate a third embodiment of a compression garment apparatus 220 of the present invention. The compression garment apparatus 220 is similar to the compression garment apparatus 20 described above, and corresponding parts are generally indicated by the same reference numbers, plus 200. In this embodiment, first and second support bladders 228A, 228B are provided. The support bladders 228A, 228B "frame" the knee. The first support bladder 228A includes a first portion 228A' extending circumferentially about the leg along the top of the calf to "suspend" the garment 222 about the top of the calf when the first support bladder is pressurized. The second support bladder 228B includes a first portion 228B' extending circumferentially about the leg along the top of the patella to "suspend" the garment 222 about the top of the patella when the second support bladder is pressurized. These first portions 228A', 228B' prevent undesired movement of the compression garment 222 longitudinally with respect to the leg L. The first and second support bladders 228A, 228B also include respective second portions 228A", 228B" extending along the length of the leg L adjacent the inner and outer sides of the knee, respectively. These second portions 228A", 228B" assist in preventing undesired movement of the compression garment 222 circumferentially with respect to the leg L. In use, the pressurizer 224 may pressurize the therapeutic bladders 226A-226C and support bladders 228A, 228B as described above to maintain desired fit and maintain the therapeutic bladders in position with respect to the target compression zone T.

Having described the invention in detail, it will be apparent that modifications and variations are possible without departing from the scope of the invention defined in the appended claims.

When introducing elements of the present invention or the preferred embodiments(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A compression garment apparatus comprising:
a compression garment including an inflatable therapeutic bladder and an inflatable support bladder, the compression garment being selectively positionable on a body part so the therapeutic bladder covers a target compression zone on the body part; and
a pressurizer operatively connectable to the therapeutic bladder and the support bladder for selectively pressurizing the bladders by increasing gas pressure within the bladders, the pressurizer including:
 a sensor for sensing and generating signals representative of at least one physical characteristic selected from a group of characteristics consisting of an orientation of the body part, a motion of the body part, an acceleration of the body part, a motion of the garment relative to the target compression zone, a pressure in the therapeutic bladder, a pressure in the support bladder, a gas volume in the therapeutic bladder, and a gas volume in the support bladder; and
 a controller operatively connected to the sensor, the controller cyclically directing pressurized gas to the therapeutic bladder to provide intermittent compression therapy to the target compression zone on the body part and non-cyclically directing pressurized gas to the support bladder in response to signals received from the sensor representing the physical characteristic to maintain the therapeutic bladder in position with respect to the target compression zone.

2. A compression garment apparatus as set forth in claim 1, wherein the controller directs pressurized gas to the support bladder in response to a signal received from the sensor indicating the orientation of the body part is outside a predetermined orientation range.

3. A compression garment apparatus as set forth in claim 1, wherein the controller directs pressurized gas to the support bladder in response to a signal received from the sensor indicating the motion of the body part is beyond a threshold amount of motion.

4. A compression garment apparatus as set forth in claim 1, wherein the controller decreases gas pressure in the support bladder by venting gas from the support bladder in response to a signal received from the sensor representing the orientation of the body part being recumbent.

5. A compression garment apparatus as set forth in claim 1, wherein the controller directs pressurized gas to the support bladder in response to a signal received from the sensor indicating the acceleration of the body part is outside a predetermined acceleration range.

6. A compression garment apparatus as set forth in claim 1, wherein the controller prevents gas pressure in the support bladder from exceeding a pressure at which the support bladder is generally compliant to movement of the body part.

7. The compression garment apparatus of claim 1, wherein:
the inflatable therapeutic bladder consists of three separate therapeutic bladders arranged in sequence on the compression garment; and
the controller sequentially directs pressurized gas to each therapeutic bladder to provide intermittent compression therapy to the target compression zone on the body part to peristaltically enhance flow of bodily fluids in the body part.

8. A method of providing compression therapy to a target compression zone of a body part of a human comprising:
covering the target compression zone of the body part with a compression garment having an inflatable therapeutic bladder and an inflatable support bladder;
sensing at least one characteristic selected from a group of characteristics consisting of an orientation of the body part, a motion of the body part, an acceleration of the body part, a motion of the garment relative to the target compression zone, a pressure in the therapeutic bladder, a pressure in the support bladder, a gas volume in the therapeutic bladder, and a gas volume in the support bladder;
non-cyclically pressurizing the support bladder in response to the sensed characteristic to maintain the therapeutic bladder in position with respect to the target compression zone; and
cyclically pressurizing the therapeutic bladder to provide intermittent compression therapy to the target compression zone of the body part.

9. A method as set forth in claim 8, wherein the body part is a limb having a longitudinal axis and the support bladder is pressurized in response to sensing the orientation of the body part being at least 30 degrees with respect to horizontal.

10. A method as set forth in claim 8, wherein the body part is a leg and the support bladder is pressurized in response to sensing the orientation of the leg being generally upright.

11. A method as set forth in claim 8, wherein the body part is a leg and the support bladder is pressurized in response to sensed motion of the leg indicating the human is ambulating.

12. A method as set forth in claim 8, further comprising reducing pressure in the support bladder in response to sensing the orientation of the body part being outside a predetermined orientation range.

13. A method as set forth in claim 8, wherein the support bladder is pressurized in response to the acceleration of the body part being outside a predetermined acceleration range.

14. A method as set forth in claim 8, further comprising preventing pressure in the support bladder from exceeding a pressure at which the support bladder is generally compliant to movement of the body part.

15. A method as set forth in claim 8, wherein the inflatable therapeutic bladder consists of three separate therapeutic bladders arranged in sequence on the body part and the step of cyclically pressurizing the therapeutic bladder comprises sequentially pressurizing each of the therapeutic bladders.

16. A compression garment apparatus comprising:
an inflatable therapeutic bladder sized and shaped for covering a target compression zone on a body part;
an inflatable support bladder connected to the therapeutic bladder for holding the therapeutic bladder in position with respect to the target compression zone; and
a pressurizer operatively connected to the therapeutic bladder and the support bladder, the pressurizer non-cyclically pressurizing the support bladder to hold the therapeutic bladder in position while selectively cyclically pressurizing the therapeutic bladder to provide intermittent compression therapy to the target compression zone on the body part.

17. A compression garment apparatus as set forth in claim 16, wherein the pressurizer includes a sensor for sensing and generating signals representative of at least one physical characteristic selected from a group of characteristics consisting of an orientation of the body part, a motion of the body part, an acceleration of the body part, a motion of the therapeutic bladder relative to the target compression zone, a pressure in the therapeutic bladder, a pressure in the support bladder, a gas volume in the therapeutic bladder, and a gas volume in the support bladder; and the pressurizer selectively pressurizes the support bladder based at least in part on said signals.

18. A compression garment apparatus as set forth in claim 16, wherein the support bladder is positioned relative to the therapeutic bladder and sized and shaped to extend longitudinally along the body part when the therapeutic bladder is in position covering the target compression zone on the body part.

19. A compression garment apparatus as set forth in claim 16, wherein the support bladder is positioned relative to the therapeutic bladder and sized and shaped to extend circumferentially around the body part when the therapeutic bladder is in position covering the target compression zone on the body part.

20. A compression garment apparatus as set forth in claim 16, wherein the therapeutic bladder comprises a plurality of separate therapeutic bladders for sequentially providing pressure to the target compression zone on the body part.

21. A compression garment apparatus as set forth in claim 1, wherein the sensor comprises at least one orientation, motion, acceleration, or position sensor for sensing and generating signals representative of at least one physical characteristic selected from a group of characteristics consisting of an orientation of the body part, a motion of the body part, and a motion of the garment relative to the target compression zone.

22. A compression garment apparatus as set forth in claim 1, wherein the controller directs compressed gas to adjust a predetermined pressure in the support bladder in response to signals received from said sensor.

23. A method as set forth in claim 8, wherein sensing the at least one characteristic comprises sensing using at least one sensor comprising an orientation, motion, acceleration, or position sensor.

24. A method as set forth in claim 8, wherein pressurizing the support bladder comprises adjusting a predetermined pressure in the support bladder in response to the characteristic sensed by the at least one sensor.

* * * * *